US 7,358,094 B2

(12) United States Patent
Bell et al.

(10) Patent No.: US 7,358,094 B2
(45) Date of Patent: Apr. 15, 2008

(54) SENSOR SYSTEM FOR SACCHARIDES

(76) Inventors: Michael L. Bell, 2931 Hickory Pl., Fullerton, CA (US) 92835; Tony D. James, University of Bath, Department of Chemistry, Bath (GB) BA2 7AY; Susumu Arimori, 943-2-303 Kayanomori, Iizuka, Iizuka, Fukuoka (JP) 820-0011

( * ) Notice: Subject to any disclaimer, the term of this patent is extended or adjusted under 35 U.S.C. 154(b) by 670 days.

(21) Appl. No.: 10/427,404

(22) Filed: May 1, 2003

(65) Prior Publication Data
US 2004/0219535 A1 Nov. 4, 2004

(51) Int. Cl.
*G01N 21/76* (2006.01)
*C12Q 1/68* (2006.01)
*G01N 33/00* (2006.01)

(52) U.S. Cl. .................... 436/172; 436/94; 422/50
(58) Field of Classification Search ............ 435/14; 436/14, 94; 422/50

See application file for complete search history.

(56) References Cited

U.S. PATENT DOCUMENTS

| 4,496,722 | A |   | 1/1985  | Gallop et al. |
|-----------|---|---|---------|---------------|
| 4,609,689 | A | * | 9/1986  | Schwartz et al. ......... 523/202 |
| 5,156,972 | A | * | 10/1992 | Issachar ..................... 422/68.1 |
| 5,212,099 | A |   | 5/1993  | Marcus |
| 5,342,789 | A |   | 8/1994  | Chick et al. |
| 5,501,949 | A |   | 3/1996  | Marshall |
| 5,503,770 | A |   | 4/1996  | James et al. |
| 5,512,659 | A | * | 4/1996  | Ullman et al. ........... 530/391.1 |

(Continued)

FOREIGN PATENT DOCUMENTS

DE 44 39 783 4/1996

(Continued)

OTHER PUBLICATIONS

International Search Report, PCT/US2004/013245.

(Continued)

*Primary Examiner*—Jill Warden
*Assistant Examiner*—Neil Turk
(74) *Attorney, Agent, or Firm*—Michael C. Schiffer

(57) ABSTRACT

An analytical system for detecting a saccharide is provided. The analytical system includes a saccharide sensor attached to a solid substrate and having the formula:

$$Z-(CH_2)_n-N\begin{array}{c}(CH_2)_m-Bd_1\\ \\Sp\\ \\N-(CH_2)_x-An-Substrate\\ \\(CH_2)_y-Bd_2\end{array}$$

Where Z is selected from the group consisting of hydrogen, alkyl groups, an aryl; N is a nitrogen atom; $B_{d1}$ and $B_{d2}$ are independently selected binding groups, wherein the binding groups are capable of binding an saccharide; Sp is a spacer; An is an anchor group for attaching the sensor to solid substrate, including a bead; and n=1 or 2, m=1 or 2, y=1 or 2, and p is an integer. In one embodiment the saccharide sensor preferentially detects glucose. The invention further provides beads having the saccharide sensor attached thereto and methods of detecting glucose using the system.

22 Claims, 4 Drawing Sheets

U.S. PATENT DOCUMENTS

| | | | |
|---|---|---|---|
| 5,763,238 | A | 6/1998 | James et al. |
| 5,798,083 | A | 8/1998 | Massey et al. |
| 6,002,954 | A | 12/1999 | Antwerp et al. |
| 6,130,094 | A * | 10/2000 | Waggoner et al. ............ 436/63 |
| 6,163,714 | A * | 12/2000 | Stanley et al. ............. 600/316 |
| 6,366,793 | B1 | 4/2002 | McNeal |
| 6,387,672 | B1 | 5/2002 | Armiro et al. |
| 2002/0119581 | A1 | 8/2002 | Daniloff |
| 2002/0127626 | A1 | 9/2002 | Daniloff |
| 2003/0207461 | A1 * | 11/2003 | Bell et al. .................. 436/172 |

FOREIGN PATENT DOCUMENTS

| | | |
|---|---|---|
| EP | 0 729 962 | 9/1996 |
| WO | WO 02/054067 | 7/2002 |
| WO | WO 02/057788 | 7/2002 |
| WO | WO 03/042698 | 5/2003 |

OTHER PUBLICATIONS

Sandanayake et al, *Two Dimensional Photoinduced Electron Transfer (PET) Fluorescence Sensor for Saccharides*, Chem. Letters (1995) 503-505.

James et al., *Novel Saccharide-Photoinduced Electron Transfer Sensors Based on the Interaction of Boronic Acid and Amine*, J. Am. Chem. Soc. vol. 117, No. 35, (21995) 8982-8987.

Takeuchi, et al., *Fluorescence and CD Spectroscopic Sugar Sensing by A Cyanine-appended Diboronic Acid Probe*, Tetrahedron, vol. 52, No. 4, pp. 1195-1204.

Hartley, et al, *Synthetic Receptors*, J. Chem. Soc., Perkin Trans. 1, 2000, pp. 3155-3184.

Arimori et al., Abstract XP-002210937, *Modular Fluorescence Sensors for Saccharides*, Royal Society of Chemistry (2001), vol. 18, 1836-1837.

Aime, S. et al., "Synthesis and Characterization of a Novel DTPA-like Gadolinium(III) Complex: A Potential Reagent for the Determination of Glycated Proteins by Water Proton NMR Relaxation Measurements," Inorg. Chem., (1993), pp. 2068-2071, vol. 32, No. 10.

Arimori, S. et al., "A modular electrochemical sensor for saccharides," Chemical Communications, (2002), pp. 2368-2369, vol. 20.

Supplementary European Search Report, dated Apr. 21, 2006.

Arimori, S. et al., "Modular fluorescence sensors for saccharides," J. Chem. Soc,, Perkin Trans. 1, (2002), pp. 803-808.

\* cited by examiner

PARTICLES FOR USE IN A DETECTION SYSTEM

SENSOR SYSTEM FOR SACCHARIDES

CROSS REFERENCE TO RELATED APPLICATION

This application is related to U.S. Pat. No. 6,387,672, the contents of which are hereby incorporated by reference in their entirety.

BACKGROUND OF THE INVENTION

The following description provides a summary of information relevant to the present invention and is not a concession that any of the information provided or publications referenced herein is prior art to the presently claimed invention.

1. Area of the Art

The invention relates generally to fluorescence sensor molecules and specifically to a new group of modular fluorescence sensor molecules.

2. Description of the Prior Art

Numerous assay methods have been developed for the detection and quantitative determination of analytes contained in biochemical samples. A substantial portion of the currently used assay methods relies on specific binding reactions between analytes and assay reagents. The analytes may be large complex molecules, such as proteins, viruses, viral antigens, bacterial cells, cell surface receptors, enzymes, hormones, polysaccharides, glycoproteins, lipoproteins, or small haptenic molecules, such as peptides, certain hormones, therapeutic drugs, and drugs of abuse, to name a few.

The binding assays can be divided into two major groups based on their format: homogeneous and heterogeneous assays. Homogeneous assays are based on a single-phase reaction between analyte and assay reagents. Heterogeneous assays, typically, involve binding of an analyte contained in the liquid sample to assay reagents, which are attached to a solid support. Various materials have been used as support surfaces, including glass rods, glass beads, silica impregnated strips, glass fiber, and microparticles.

Dyes in general, and fluorescent dyes in particular, are commonly utilized in both homogeneous and heterogeneous binding assays to provide a detectable signal. However, an accurate detection of fluorescent signals produced by analytes bound to the labels is often hindered by a high and variable background due to the fluorescence of the biological sample itself.

Liquid flow cytometry helps to overcome this problem. In flow cytometry, labeled particles with bound analyte are passed through a laser beam. The emitted fluorescent signals of the particles are measured and correlated to the presence and quantity of the analyte. The main advantage of this method is its capability of accurate detection and measurement of the fluorescent signals associated with the bound analyte in the presence of other unbound constituents of the sample.

Saccharides represent an important group of biochemical analytes. Current methods for determining their concentrations in a sample typically rely on enzymatic assays. Although enzymatic assays have proven to be reliable, they must utilize rather unstable enzymes, which become exhausted in the presence of their substrates. Additionally, conventional enzymatic assay methods cannot be utilized in a convenient flow cytometry format. Particle-based assays, such as the ones used in flow cytometry, require a signal change confined to the particle. Normal enzymatic analysis methods use freely diffusable intermediates that violate this requirement.

Determination of saccharides is particularly important in clinical settings. Treatment of diabetes and hypoglycemia requires frequent measurement of tissue glucose concentration. This is commonly accomplished by drawing a small blood sample (as by a fingerstick) several times daily. A patient typically uses a lancet to draw a droplet of blood and applies the droplet to a reagent strip which is read in a small meter. This process is painful, invasive, and time-consuming.

Recently, a minimally invasive method for measuring glucose in vivo has been disclosed in U.S. patent application Ser. No. 09/393,738 filed on Sep. 10, 1999, which has been commonly assigned to the assignee of the present invention and is incorporated by reference herein. The method is based on the use of implanted sensor particles capable of generating a detectable analyte signal in response to the analyte concentration in the body. The proposed method is less intrusive than the conventional fingerstick technique for measuring blood D-glucose. It requires only periodical replacement of the sensor particles in the skin.

The sensor particles typically comprise fluorescence sensors either attached to the surface or incorporated into the body of the particles. The sensors are specific to the target analyte. The binding of the sensor to the analyte generates a detectable signal that is responsive to the concentration of the analyte. When the analyte is glucose, diboronic acids conjugated to fluors are used.

Similar fluorescent sensors, which are specific to glucose, are also described by James et al., in the Journal of the American Chemical Society, 1995, vol. 117 pp. 8982-8987, by James et al. in U.S. Pat. No. 5,503,770, and by Takeuchi et al. in Tetrahedron, vol. 52, No. 4, pp. 1195-1204. Briefly, the fluorescent sensors of James and Takeuchi have the following general formula:

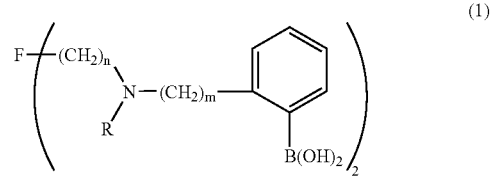

(1)

In the formula, F designates a fluorophore, R is a lower aliphatic or aromatic group, and n+m is 2 or 3. The fluorescent intensity of the sensor changes in response to photo-induced electron transfer (PET) between the amine group and the fluorophore as modulated by binding of glucose hydroxyls to a pair of boronic acids. In the absence of glucose binding, the fluorescence by the fluorescent group is quenched by the unshared electron pair of the nitrogen atom. When glucose is bound, the unshared electron pair is utilized in the bond formation and does not participate in fluorescence-quenching. Consequently, intrinsic fluorescence of the sensor is expressed.

SUMMARY OF THE INVENTION

While an application of above-described fluorescent sensors in biochemical assays and clinical tests provide certain advantages over earlier enzyme-based in vitro methods, it, nevertheless, suffers from serious shortcomings. Because the fluorophore is used as a spacer to separate the saccharide binding groups and to provide desired analyte selectivity, strict limitations on the type of the fluorophore, its size and conformation are imposed. For the same reason, there are also significant limitations on the type, size, and conformation of analyte that can specifically bind to the disclosed fluorescent compounds to produce a detectable signal. Furthermore, although the referenced art suggests using the PET-type fluorescent compounds in a heterogeneous assay format, no means for attaching the compound to a solid support are provided. Again, such attachment would be particularly difficult in view of the strict limitations imposed on the conformation and structure of the fluorescent molecule.

Accordingly, it is an object of the present invention to provide a fluorescent sensor, particularly PET-type sensor, with a modular structure, which allows independent selection of fluorescent and binding groups. It is also an object of the present invention to provide a fluorescent sensor that can be easily adapted for specific binding to a broad range of analytes. It is a further object of the present invention to provide a fluorescent sensor that can be used in both homogeneous and heterogeneous binding assay formats and can be easily attached to solid surfaces. Finally, it is an object of the present invention to provide convenient methods of making and using the fluorescent sensors.

These and other objects and advantages are achieved in a modular fluorescence sensor of the present invention having the following general formula:

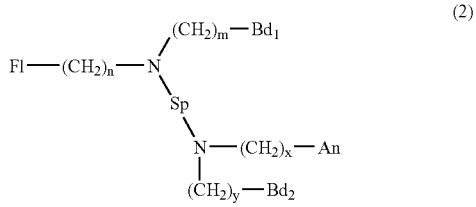

(2)

In the above formula, Fl is a fluorophore, N is a nitrogen atom, Bd1 and Bd2 are independently selected binding groups, Sp is an aliphatic spacer, and An is an anchor group for attaching the sensor to solid substrates. n=1 or 2, m=1 or 2, y=1 or 3, and x is an integer. The binding groups are capable of binding an analyte molecule to form a stable 1:1 complex. Examples of binding groups include, but are not limited to, boronic acid, crown ether, and aza-crown ether, such as 1,4,7,10,13-Pentaoxa-16-aza-cyclooctadecane (aza 18-crown-6) and 1,4,7,13-tetraoxa-10-aza-cyclohexadecane (aza 15-crown-5). In a preferred embodiment, the Bd1 is R1—B(OH)2 and $B_{d2}$ is R2—B(OH)2. R1 and R2 are aliphatic or aromatic functional groups selected independently from each other and B is a boron atom.

Preferably Sp contains 6 carbon atoms.

In another aspect, the present invention provides a method of synthesizing a modular fluorescence sensor. The method comprises the steps of:

(a) forming an asymmetric compound of the following general formula:

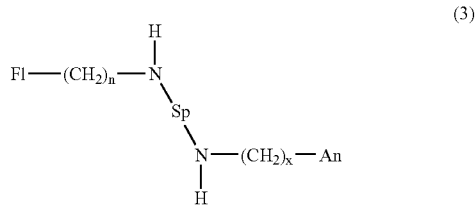

(3)

and (b) replacing hydrogen atoms with $B_{d1}$ and $B_{d2}$ groups.

In the above formula, Fl is a fluorophore, N is a nitrogen atom, H is a hydrogen atom, Sp is an aliphatic spacer, and An is an anchor group for attaching the sensor to solid substrates. $B_{d1}$ and $B_{d2}$ are independently selected binding groups capable of binding an analyte molecule to form a stable 1:1 complex, n=1 or 2, and x is an integer.

The present invention also provides a method of labeling solid substrates. The method comprises the steps of:

(a) providing a solid substrate;
(b) providing a modular fluorescence sensor of the present invention of formula (2), wherein An is capable of being attached to the solid substrate;
(c) reacting the sensor with the solid substrate under a condition sufficient to attach the sensor to the substrate.

The solid substrate may be, for example, a bead, particle, or micro particle. Where the sensor is attached to a bead, it may be attached to the outer surface of the bead or it may be bound to the inside of the bead.

The present invention also provides an analytical system for detecting a saccharide comprising:

a) a sample known to contain or suspected of containing a saccharide;
b) one or more than one solid substrate, the solid substrate having attached thereto one or more than one saccharide sensor having the formula:

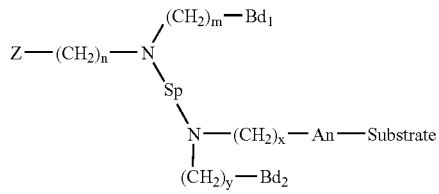

In the above formula Z is selected from the group consisting of hydrogen, alkyl groups, aryl groups; N is a nitrogen atom; $B_{d1}$ and $B_{d2}$ are independently selected binding groups, wherein the binding groups are capable of binding an analyte molecule to form a stable 1:1 complex; Sp is an aliphatic spacer; An is an anchor group for attaching the sensor to the solid substrate; and n=1 or 2, m=1 or 2, y=1 or 2, and x is an integer; and c) means for detecting the at least one of saccharides that is bound or not bound to the sensor. In one embodiment the system selectively detects glucose.

The modular fluorescence sensor of the present invention has been found to provide a number of advantages. The modular structure of the sensor allows a convenient replacement of its functional parts to fit analytes within a broad range of structures, binding affinities, and solubilities. The anchor site and the asymmetrical structure of the instant sensor permit a convenient attachment of the sensor to a variety of solid substrates, as required in heterogenic assay formats. Also, the fluorescent sensor of this invention couples the signal generation to the analyte binding and thereby localizes the measurement of an analyte. Consequently, the sensor is well suited for applications in particle-based assays and flow cytometry. Finally, in the present invention, a special spacer group is used to provide the desired intramolecular distance between analyte-binding groups, which governs the analyte selectivity. The conventional PET-type sensors, on the other hand, utilize a fluorophore as a spacer, which puts stringent limitations on the type of fluorophore that can be used. On the contrary, in the present invention, the fluorophore may be selected without limitations to its size or conformation.

The invention further includes a non-fluorescent saccharide sensor. This non-fluorescent saccharide sensor is attached to a bead in one embodiment. This embodiment is useful for methods of detecting saccharides in competitive assays. In one embodiment, the method selectively detects glucose.

In view of its versatility, the novel fluorescent sensor of the present invention is useful in a broad range of analytical and clinical applications. The sensor is particularly beneficial in the detection and qualitative analysis of saccharides.

DESCRIPTION OF THE FIGURES

The above-mentioned and other features of this invention and the manner of obtaining them will become more apparent, and will be best understood by reference to the following description, taken in conjunction with the accompanying drawings. These drawings depict only typical embodiments of the invention and do not therefore limit its scope.

DETAILED DESCRIPTION OF THE INVENTION

Figure 1:
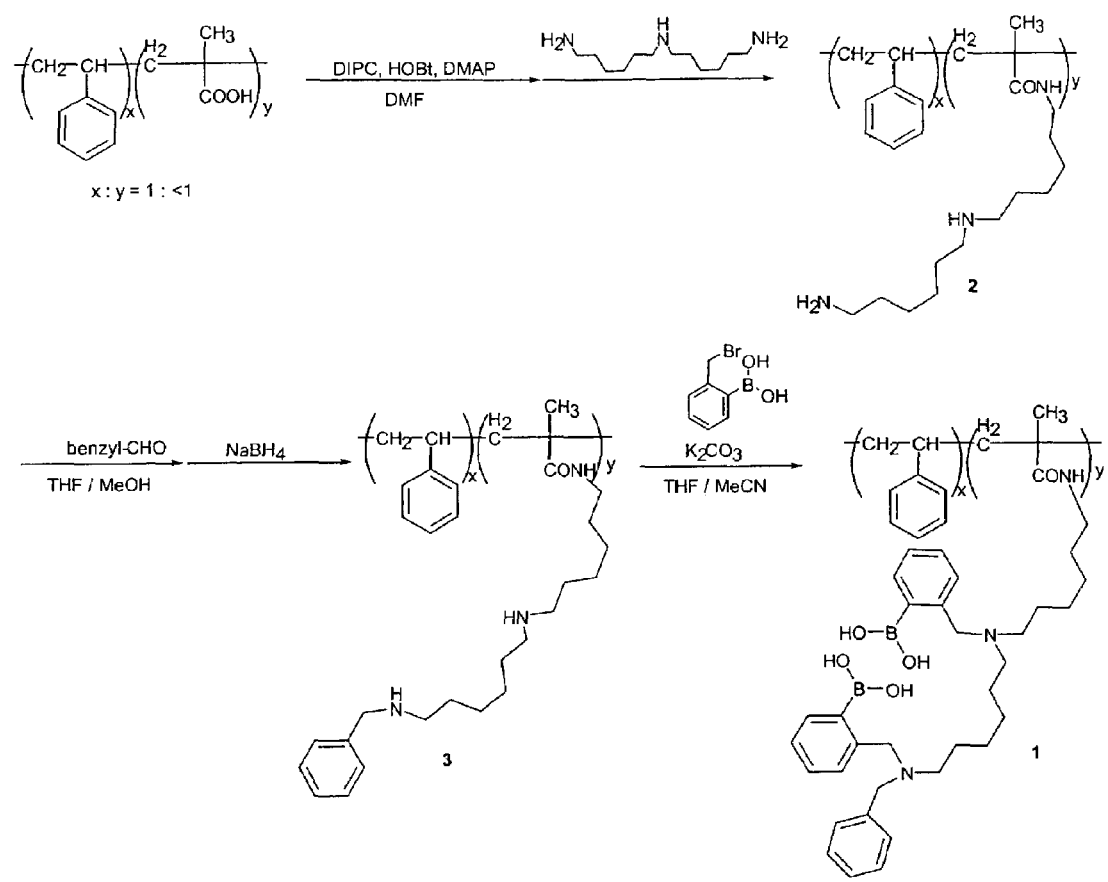
FIG. 1 illustrates the synthesis of a saccharide sensor of the invention onto a bead based solid substrate.

The present invention provides a modular fluorescence sensor having the following general formula:

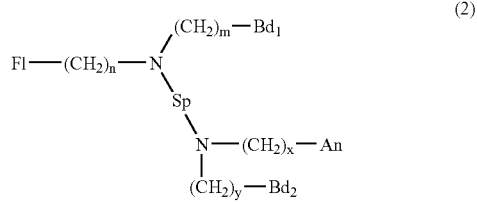

(2)

In the above formula, Fl is a fluorophore, N is a nitrogen atom, $B_{d1}$ and $B_{d2}$ are independently selected binding groups, Sp is an aliphatic spacer, and An is an anchor group for attaching the sensor to solid substrates. In the formula (2), n, m, x, and y are integers, where n=1 or 2, m=1 or 2, and y=1 or 2, and x is an integer. In one embodiment, x=0-10. The binding groups are capable of binding an analyte molecule to form a stable 1:1 complex.

In the present invention, the fluorophore Fl does not act as a spacer between binding groups. Consequently, it can be selected from a broad range of functional groups having various sizes and conformations. Examples of acceptable fluorophores include, but are not limited to, functional groups containing π-electron systems, such as naphtyl, anthryl, pyrenyl, phenanthryl, and perylenyl. The fluorophore may be unsubstituted or substituted. For example, it is well known that certain molecules can be rendered water-soluble by the introduction into the molecule of a strong basic or acidic group, such as carboxylic acid or sulfonic acid. Consequently, the fluorophore may be substituted with sulfonic acid group(s) to accommodate homogeneous assay formats.

Although embodiments of the sensor contain a fluorophore in its molecular structure, it does not emit fluorescence in the absence of the analyte. As explained in the Introduction, in PET molecules, the fluorescence of the fluorophore is quenched by the unshared electron pair of the nitrogen atom(s). When the sensor binds the analyte contained in a sample, the unshared electron pair of the nitrogen atom participates in the formation of an intramolecular complex of the sensor and the analyte. Consequently, the intrinsic fluorescence of the sensor becomes expressed.

In the present invention, the binding groups may be any functional groups, as long as they provide the desired specific binding of the analyte to the sensor with a formation of 1:1 complex. The binding groups are preferably electron deficient groups. The electron deficiency governs the shift of the unshared electron pair from the nitrogen atoms to the binding group when specifically binding the analyte. Examples of the acceptable binding groups include, but are not limited to, boronic acid, crown ether, and aza-crown ether, such as 1,4,7,10,13-Pentaoxa-16-aza-cyclooctadecane (aza 18-crown-6) and 1,4,7,1 3-tetraoxa-10-aza-cyclohexadecane (aza 15-crown-5). Examples of analytes that may be identified by utilizing sensors of the present invention include, but are not limited to, saccharides, amino saccharides, and carbonyl saccharides.

In a preferred embodiment, the $B_{d1}$ is $R_1$—$B(OH)_2$ and $B_{d2}$ is $R_2$—$B(OH)_2$. $R_1$ and $R_2$ are aliphatic or aromatic functional groups selected independently from each other, and B is a boron atom. Examples of acceptable R1 and R2 groups include, but are not limited to, methyl, ethyl, propyl, butyl, phenyl, methoxy, ethoxy, butoxy, and phenoxy groups.

The binding groups are separated by the aliphatic spacer Sp. The length of the carbon backbone of the spacer is selected to match the size of the analyte. In one embodiment, where the analyte is glucose, the length of the carbon backbone is such that distance between binding groups is comparable with the size of glucose.

Although the spacer may have a straight, branched, or cyclic structure, in the preferred embodiment the spacer is a straight-chain alkane. Typically, the spacer comprises from 1 to 9 carbon atoms, but spacers of larger length may be also used to match the size of the analyte. For example, when the analyte is glucose, the spacer may comprise six carbon atoms.

The anchor group An of the sensor provides means for immobilization of the sensor on a solid substrate/support, for example on a substrate used in heterogeneous binding assay. The terms solid substrate, solid support, substrate, and support are used interchangeably herein. The An group is attached to one of the nitrogen atoms of the sensor either directly or by means of a carbon bridge —$(CH_2)_x$—. The type of An group and the number of carbons (x) in the carbon bridge are selected to provide a secure attachment of the sensor to the solid substrate. For example, in one embodiment, the sensor is attached to a micrometer scale bead. The micrometer scale beads with the attached sensor of the present invention may be used in various applications, including flow cytometry. Typically, An comprises an organic functionality. In one embodiment An comprises phenyl.

The anchor group An is optional. For example, in homogeneous assays, no attachment of the sensor is required. Therefore, the sensor may be synthesized without anchor group or with a functional group, such as methyl and benzyl.

This invention provides a framework for modular sensors that have a minimal interaction between their functional elements. Individual functional elements of the sensor of the present invention may be easily replaced to accommodate a broad range of analytes. For example, in one embodiment, all functional groups of the sensor and the length of carbon bridges are selected to provide selective binding of the sensor to glucose.

Preferably, a modular fluorescence sensor of the present invention has the following general formula:

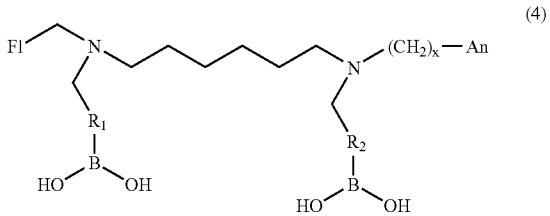

(4)

In the above formula (4), Fl is a fluorophore, N is a nitrogen atom, and B is a boron atom. $R_1$ and $R_2$ are aliphatic or aromatic functional groups which allow covalent binding of an analyte with the hydroxyls of boronic acid functionalities to form a stable 1:1 complex. $R_1$ and $R_2$ are selected independently from each other. An is an anchor group for attaching the sensor to a solid substrates; and x is any integer. In one embodiment, x=0-10.

A typical compound falling within the formulas (2) and (4) of the present invention has the following formula:

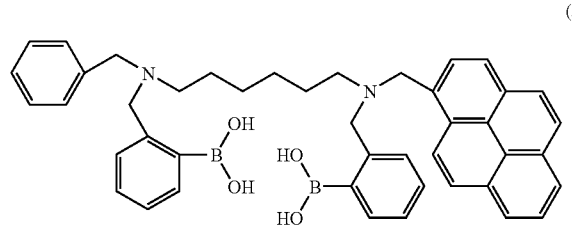

(5)

Unexpectedly, the compound (5) has a specific sensitivity to glucose and emits a strong fluorescence when binding to glucose contained in a sample. Such specificity to glucose can be explained by the structure of the compound (5). Two boronic acid groups are separated from each other by a spacer comprising a six-carbon chain, which allows them to bind cis-1,2- and 4,6-hydroxyl groups of glucose and form a strong 1:1 complex with glucose.

In another aspect, the present invention provides a method of synthesizing a modular fluorescence sensor. The method comprises the steps of:

(a) forming an asymmetric compound of the following general formula:

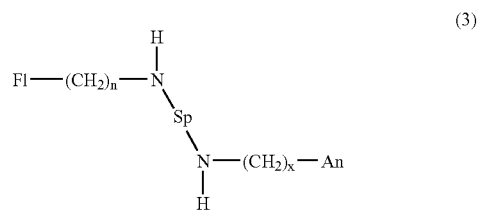

(3)

and (b) replacing hydrogen atoms with $B_{d1}$ and $B_{d2}$ groups.

In the above formula, Fl is a fluorophore, N is a nitrogen atom and H is a hydrogen atom, Sp is an aliphatic spacer, and An is an anchor group for attaching the sensor to solid substrates. $B_{d1}$ and $B_{d2}$ are independently selected binding groups capable of binding an analyte molecule to form a stable 1:1 complex, n=1 or 2, and x is any integer. In one embodiment, x=0-10. In one embodiment, the step of replacing hydrogen atoms comprises adding orthobromomethyl phenylboronic acid. For instance, a reaction scheme such as one shown in FIG. 1 and discussed in detail in Example 1 below may be utilized.

The present invention also provides a method of labeling solid substrates. The method comprises the steps of:

(a) providing a solid substrate;
(b) providing a modular fluorescence sensor of the present invention of formula (2), wherein An is capable of being attached to the solid substrate;
(c) reacting the sensor with the solid substrate under a condition sufficient to attach the sensor to the substrate.

For the purpose of the present invention, a condition is sufficient if it does not hinder attachment of the sensor to the substrate. Those skilled in the art will know what conditions should be sufficient based on the type of the solid substrate and the nature of the anchor group. For example, when the anchor group is amino, preferably primary amine, the solid substrate should contain carboxylic acid group, and the sufficient condition is satisfied by addition of a coupling agent. Acceptable coupling agents include, but are not limited to, 1,3-dicyclohexylcarbodimide (DCC), 1-ethyl-3-(3-dimethylaminopropyl)carboimide or water soluble carboimide, and carbonyldiimidazole (CDI). Additionally, N-hydroxysuccinimide may be added to the reaction mixture to obtain better reaction efficiency. In accordance with one embodiment of the present invention, when the anchor group is primary amine, the sensor is attached to the substrate by mixing 1,3-disopropylcarbodiimide (DIPC), 1-hydroxy-1H-benzotriazole (HOBt), 4-N,N-dimethylaminopyridine (DMAP) with N,N-dimethylformamide (DMF) as solvent, and stirring the mixture at room temperature for 2-24 hours.

The present invention also provides a saccharide sensor attached or immobilized to solid substrates such as beads. It is not required that the saccharide sensor contain a fluorophore in its molecular structure in this embodiment. A saccharide sensor attached to a solid substrate can have the formula:

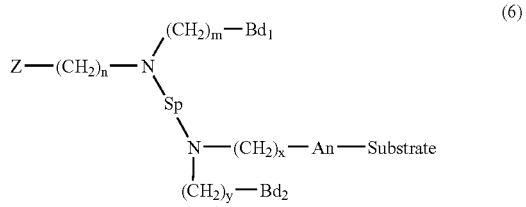
(6)

In the above formula, Z is selected from the group consisting of hydrogen, alkyl groups, aryl groups, and fluorophores, N is a nitrogen atom, $B_{d1}$ and $B_{d2}$ are independently selected binding groups, Sp is an aliphatic spacer, An is an anchor group for attaching the sensor to a solid substrate. In the formula (6), n, m, x, and y are integers, where n=1 or 2, m=1 or 2, and y=1 or 2, and x is an integer. In one embodiment, x=0-10. In one embodiment, the binding groups are capable of binding an analyte molecule to form a stable 1:1 complex.

In one embodiment, the saccharide sensing bead has a saccharide sensor that selectively binds and detects glucose which has the following structure:

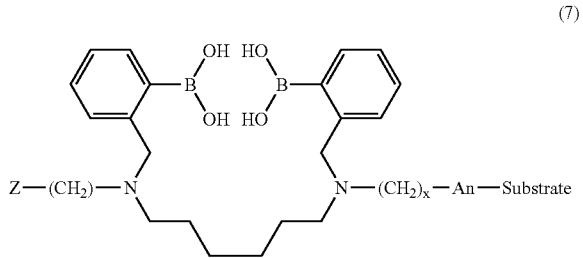
(7)

In the above formula, Z is selected from the group consisting of hydrogen, alkyl groups, aryl groups, N is a nitrogen atom, An is an anchor group for attaching the sensor to a solid substrate, and x is an integer. Z can be a fluorophore.

In another embodiment, the saccharide sensing bead comprises one or more sensors that selectively bind glucose in order to detect glucose. The sensor/ligand that is attached to the bead can have the following structure:

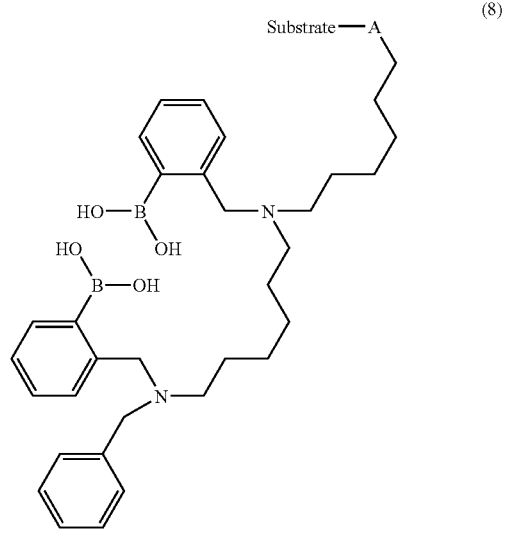
(8)

The glucose sensor shown in formula (8) does not produce an optically detectible fluorescent signal upon binding glucose. The preparation of this compound is described and illustrated in detail in Example III and FIG. 1.

The solid substrate may be a bead, particle, micro particle, or the like, and the terms bead, particle, and micro particle are used interchangeably herein. The saccharide sensing beads typically have diameters in the range of from about 0.1 to about 50 micrometers. In one embodiment of the present invention, the beads are in a size range from about 0.1 to about 20 micrometers. The beads are typically suspended in a liquid such that their density is within the range of between about 0.5 to about 2 grams per milliliter. The combination of these size and density ranges allow the saccharide sensing beads to be treated as simple liquids by most fluid transfer apparatus such as pipettes, pumps, and certain valves.

The beads are preferably round and uniform, such as commonly available polystyrene latex beads formed by emulsion polymerization. They may be produced of other materials and by other processes that are known in the art. The beads can incorporate means, such as similar charge, that effectively prevent interaction with other particulate sensors. Examples of the materials and methods include, but are not limited to, plasticized polyvinyl chloride (PVC) beads produced by droplet casting of dissolved polymers or glass-like beads produced from sol gels. In addition, the sensor beads may be made of a bio-resorbable polymer. Examples of a bio-resorbable polymer include, but are not limited to, polyglycolic acid (PGA), poly-DL-lactide-co-glycolide (PLGA), starch, gelatin, and the like.

The sensor bead of the present invention may be a hydrophilic bead such as, but not limited to, controlled pore glass (CPG) beads or a polymer gel. It may also be a hydrophobic bead with appropriate plasticizers or a sufficiently low glass transition temperature to permit free permeation by small analytes. Alternatively, it may be a semipermeable membrane such as, but not limited to, a liposome. To avoid the degradation of the sensor, the sensor may be bound to the inside of a hydrophilic bead, such as pores of CPG beads or a polymer gel. The receptors may also be captured inside a hydrophobic bead with appropriate plasticizers to permit free permeation by small analytes. The receptor may further be packaged inside the semipermeable membrane. For the purpose of the present invention, a plasticizer is appropriate if it permits free permeation of small analytes into a hydrophobic bead. Examples of such a plasticizer include, but are not limited to, dioctyl adipate, diisodecyl adipate, and the like. In accordance with an alternative embodiment, a sensor of the present invention may also be bound to the surface of hydrophobic or other insoluble beads.

Assay System

The invention further provides an analytical assay system for detecting more than one analyte at a time. This system is described in detail in copending application Ser. No. 09/990,678, filed Nov. 14, 2001, by Michael L. Bell, et al., entitled "Analyte Detection System", which is incorporated by reference in it's entirety in this application. The system utilizes fluorescent labeled beads to distinguish between numerous sub-populations of beads and quantify multiple analytes of interest. The fluorescent labels employed in the assay system can be excited by a common source and emit at distinguishable wavelengths from themselves and other fluorescent sources in the system, and have excitation wavelengths in the far-red or near-infrared region of the spectrum.

According to this embodiment of the present invention, multiple analytes are simultaneously detected and measured by combining microfluidics and fluorescent bead sensor technology. Multiple analytical reactions are isolated onto a set of micrometer scale beads, which are read individually by a device such as a flow cytometer. The device determines the identity of each set of beads and the extent to which each bead has reacted with its analyte. Each set of beads: 1) carries a unique combination of fluorescent labels to code the beads; 2) is specific to an analyte, or class of analytes of interest; and 3) contains a fluorescent dye for identifying individual analytes of interest (i.e., an analytical dye, or a fluorescent analyte detection dye).

According to the method of the present invention, an analytical sample is allowed to react with a set of beads specific to various analytes of interest. The beads are then passed through a detection device such as a flow cytometer. Beads that have reacted with their specific analyte of interest generate fluorescent emission spectra corresponding to the fluorescent dye associated with the particular bead and analyte of interest. The device identifies the beads at least partly by a unique combination of fluorescent labels incorporated into the beads. The information from the fluorescent labels is correlated with the information from the analyte specific fluorescent dye and the corresponding results allow quantitative identification of multiple analytes in one reaction.

An aspect of the detection system and methods described herein is the preparation and use of appropriately labeled beads. The beads employed in the present invention are generally made of polymeric materials such as a polystyrene. Suitable preparation techniques are generally known to those skilled in the art to make beads/particles that are useful in the present invention. An example of a suitable preparation technique is described in U.S. Pat. No. 4,609,689, incorporated herein by reference. Alternatively, the beads/particles may be obtained from a commercial supplier such as Bio-Rad Laboratories Inc., or Bangs Laboratories Inc.

The fluorescent labels employed in the invention are preferably, but not required, embedded within the bead. Internally embedding the fluorescent labels in the bead increases signal stability by shielding the labels from environmental factors that cause fluorescence degradation. Internally embedding the fluorescent labels in the bead also reserves the exterior of the bead for binding analytes and/or analytical dyes.

The fluorescent labels are added to the beads by using methods known to those in the art. One known method is a casting process, such as the casting process described in U.S. Pat. Nos. 4,302,166 and 4,162,282, which are incorporated herein by reference. In this process, a fluorescent label and a polymer are dissolved in a solvent. The solution is expelled as a stream through a fine nozzle into a sheath of water. A piezoelectric transducer breaks the stream up into discrete droplets that cure into beads as the solvent diffuses into the water. Another process is the swell-shrink method. This method, which is incorporated herein by reference, is described by L. B. Bangs (Uniform Latex Particles; Seragen Diagnostics Inc. 1984, p. 40). The swell-shrink process consists of adding an oil-soluble or hydrophobic dye to stirred beads and after an incubation period, any dye that has not been absorbed by the beads is washed away.

A set of beads is distinguishable from another set of beads on the basis of a unique combination of fluorescent labels for coding the beads. Multiple sets of beads can be used to specifically detect multiple analytes in a single reaction. Detecting multiple analytes in one reaction can simplify multiple assay procedures and result in less variability between results arising from separate assays.

In the present invention, differing amounts of fluorescent labels are used in varying combinations in different sets of beads to identify an individual set of beads from another set of beads. It is preferable, but not required, that the beads are labeled with at least two fluorescent labels and greater numbers of label combinations can be used to create greater numbers of bead populations. For example, a bead containing one part label A and two parts label B is distinguishable from a second bead containing two parts label A and one part label B. These beads are distinguishable from a third bead containing two parts label A and four parts label B or four parts label A and two parts label B. Pairs of fluorescent labels can be used in this manner to multiply the number of distinguishable bead populations. Accordingly, if an analytical detection system is capable of distinguishing ten different amounts of label A, then label A alone could be used to differentiate only ten different bead populations. However, if an analytical detection system can additionally distinguish between ten different amounts of label B, label A and label B can be used in combination to fluorescently label the identities of ten times ten, or one hundred different bead populations. If a third label is employed, the number of identifiable beads expands to one thousand distinguishable bead populations.

For an optimal number of distinct bead species it is advantageous that the emission spectra of the fluorescent bead labels accurately correspond to the concentrations of different fluorescent labels employed in particular bead sets. For accurate identification and quantification of multiple analytes on beads by fluorescence it is also advantageous that there is minimal interference between extraneous sources of fluorescence, the fluorescent labels employed in the assay, and the fluorescent dye associated with the analyte. Prior detection systems and methods have failed to provide a fluorescence based detection system that simultaneously provides these advantages.

Bead size is another parameter for coding beads. Beads may be commercially purchased in preformed sizes or prepared in different homogenous sizes. Preferred, but not required sizes of beads are 5.5, 7.0, and 10.2 microns. The size of a bead can separately be detected and determined apart from fluorescence and correlated, along with the fluorescent labels, with the analyte detection dye to detect and quantify an analyte of interest. If fewer numbers of coded beads are needed, a combination of fluorescent labels to mark beads is preferred.

The concentration of the fluorescent labels in the beads is proportional to the magnitude of the emission signal. The maximum number of distinguishable bead combinations is achieved by preparing beads with the same magnitude of emission signals. It is desirable, but not required, that the magnitude of the emission signals of different sets of beads of different sizes are of the same approximate magnitude. To achieve this objective, the concentration of fluorescent labels in small beads is increased, and/or the concentration of fluorescent labels in large beads is decreased. The emission wavelengths of the fluorescent labels used in the invention are in the near-infrared region of the electromagnetic spectrum. For purposes of this disclosure, the near infrared region of the electromagnetic spectrum is light having a wavelength greater than 750 nm and less than 1000 nm. Marking beads with fluorescent labels with longer emission wavelengths in a series of fixed predetermined amounts and the means to accomplish is an improvement in the art. The absorbance and emission spectra of these fluorescent labels are well removed from the spectra of common interferents. The long emission wavelengths of the fluorescent labels employed in the present invention enable a large selection of sensing dyes to be employed as the analytical signal for detecting multiple analytes of interest. Accordingly, fluorescent dyes having emission wavelengths less than 750 nm can be included as candidates for analytical sensing dyes without consideration of overlapping emission spectra with the fluorescent labels.

It is desirable, but not required, that the fluorescent labels be stable, both in the solvents employed for preparing the coded beads and in the beads themselves during storage and use. This includes conditions of use wherein the beads are repeatedly heated almost to the boiling point of water. Also, it is desirable, but not required, that the fluorescent labels to be employed for coding beads are soluble in the solvents required for infusing them into the beads. The fluorescent labels advantageously do not leach out of the beads during extended storage in aqueous media, or during high temperature processes employed in various assays such as DNA amplification.

It is also desirable, but not required, that the fluorescent labels in a set do not significantly interact through energy transfer, even when embedded in a single bead. Such interactions can result in inaccurate fluorescence detection (e.g., an apparent loss of fluorescence of a shorter wavelength dye in the presence of a longer wavelength dye). These types of interactions may complicate simultaneous use of the dyes as bead labels. Further, the fluorescent labels advantageously do not have significant interference with fluorescent dyes used as the analytical dye such as ETH 5294, a fluorescent pH indicator in bead optodes for measurement of target cations.

It is advantageous, but not required, that the fluorescent labels share the same excitation laser. The detection system is generally more compact when the same excitation laser is employed in the system and the use of one laser to excite the fluorescent label combination is generally more economically efficient. However, multiple excitation lasers may be employed in the detection system to excite the fluorescent label combinations in alternate embodiments.

The emission wavelengths of the fluorescent labels, when used in combination in a bead, are generally distinguishable from one another, but can have overlapping portions. A distinguishable fluorescent label combination is such that one particular bead with one combination of fluorescent labels can be identified or differentiated from another bead with a different combination of fluorescent labels by the particular emission spectra of each bead. For example, a first bead can be identified by comparing the relative magnitude of the spectral emissions of the fluorescent labels in that bead. This bead can be distinguished from a second bead that has a different relative magnitude of spectral emissions for the fluorescent labels in that bead. Fluorescent label combinations employing fluorescent labels with spectral emission peaks that differ from one another by about at least 30 nm are generally distinguishable. However, this is not a requirement of the present invention and the precise separation of the fluorescent label spectral emission maxima peaks required to practice the invention can differ with each particular combination of labels and the spectral resolution. In one embodiment, the peak wavelength of the emitted light of the analyte detection dye is different from the first and second peak wavelengths of the emitted lights of the fluorescent labels by at least 100 nm, and the first and second excitation wavelengths differ by at least 100 nm and one of the excitation wavelengths is greater than about 750 nm.

Employing the above described fluorescent labels in the assay system solves the limitations of prior fluorescence based detection systems in that: 1) the emission signals of the beads do not significantly interact with each other; 2) the analyte emission signals do not significantly interact with the emission signals of the bead; and 3) the emission signals of the beads and the analytes do not significantly interact with extraneous sources of fluorescence. In addition to the advantages recited above, the use of long wavelength fluorescers as labels permits the use of inexpensive and compact diode lasers and economical photon detectors.

Near infrared fluorescent compounds are known to those skilled in the art and can be employed in the present invention as fluorescent labels for coding particles. Suitable fluorescent compounds are selected according to the above criteria by methods known to those skilled in the art and can be employed in the present invention. For example, Webb, J. P., et al., *Eastman Organic Chemical Bulletin*, (1974), Vol. 46, No. 3; Pierce, B. M., et al., *IEEE Journal of Quantum Electronics*, (July 1982), Vol. QE-18, No. 7, pp. 1164-1170; Strekowski, et al., *J. Org. Chem.*, (1992), Vol. 57, pp. 4578-4580; and U.S. Pat. Nos., 2,887,479; 2,895,955; and 5,061,618, the disclosures of which are incorporated herein by reference, describe near infrared fluorescent compounds. In one embodiment cyanine dyes are used as fluorescent labels for coding the beads. The structures of these cyanine chromophores are described in detail in copending application Ser. No. 09/990,678.

Figures 2, 2A, 2B:
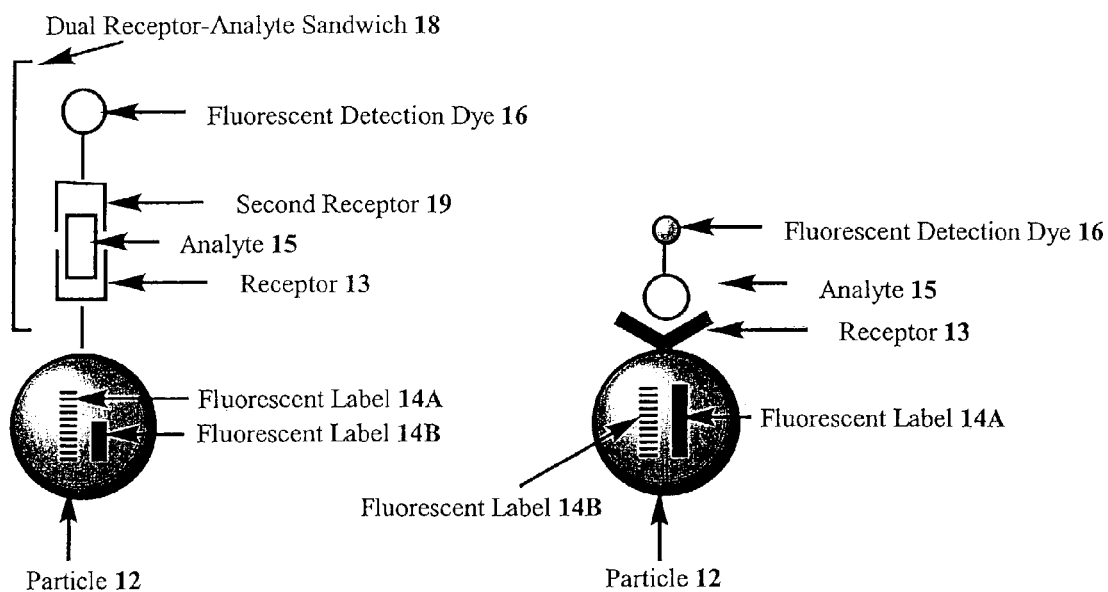
FIG. 2 is an illustration of an exemplary bead for use in a multi-analyte bead based detection system according to the present invention where bead 1 illustrates a bead-receptor-analyte-receptor complex, and bead 2 illustrates a bead-receptor-analyte complex.

Exemplary beads for use in a multi-analyte detection system are shown in FIG. 2. As illustrated in FIG. 2, beads 12 are labeled with a fluorescent labels 14A, 14B and an analyte receptor 13 is attached to the bead. The bead, 14A or 14B containing the analyte receptor 13 is then used to assay a particular sample for an analyte 15 of interest. A fluorescent analyte detection dye 16 is also present. The analyte detection dye 16 emits a fluorescent signal when the analyte specific to the receptor is also present in the sample.

Fluorescent analyte detection dyes are known to those of skill in the art. The fluorescent analyte detection dye can be a single fluorescer or a donor-receptor dye pair that is activated by energy transfer in the detection system and can be synthetic or a naturally occurring fluorescer. Appropriate fluorescent analyte detection dyes can be selected for a particular assay and used in accordance with the present invention by those of skill in the art with reference to this disclosure.

The fluorescent analyte detection dyes are complexed to the bead by various methods known to those skilled in the art depending on the particular assay employed in a specific analytical reaction. For example, the fluorescent analyte detection dye 16 can be attached to a receptor (not shown), or to an analyte 15 (FIG. 2B), or the analyte can contain a naturally occurring fluorochrome (not shown). The fluorescent analyte detection dye can also be attached to a second receptor in a dual receptor-analyte complex, (e.g., a sandwich), as exemplified in FIG. 2A.

An advantage of the assay system is that multiple analytes may be detected simultaneously in an automated system. For example, a panel of beads may be prepared, composed of multiple subpopulations of beads, where each individual subpopulation of beads is specific to a different analyte of interest. The panel of beads is allowed to react with a test sample and then passed through the detection system. In this manner, a panel of analytes may be simultaneously detected and quantified. Thus, the invention is time efficient in that multiple assays may be completed in one reaction. Examples of panels known to those skilled in the art that may be used with the invention include electrolyte panels, hormone panels, and such. It is understood that other multi-analyte panels are known to those with skill in the art, and can be employed in the detection system of the present invention, with reference to this disclosure.

A preferred assay system employed in the present detection system and methods is a flow cytometer. Flow cytometry systems are known to those in the art. A preferred flow cytometer is a modified Coulter XL flow cytometer with a 785 nm laser replacing the standard argon ion laser. The flow cytometer operates in the conventional manner known as will be understood by those with skill in the art with reference to this disclosure.

Figure 3:
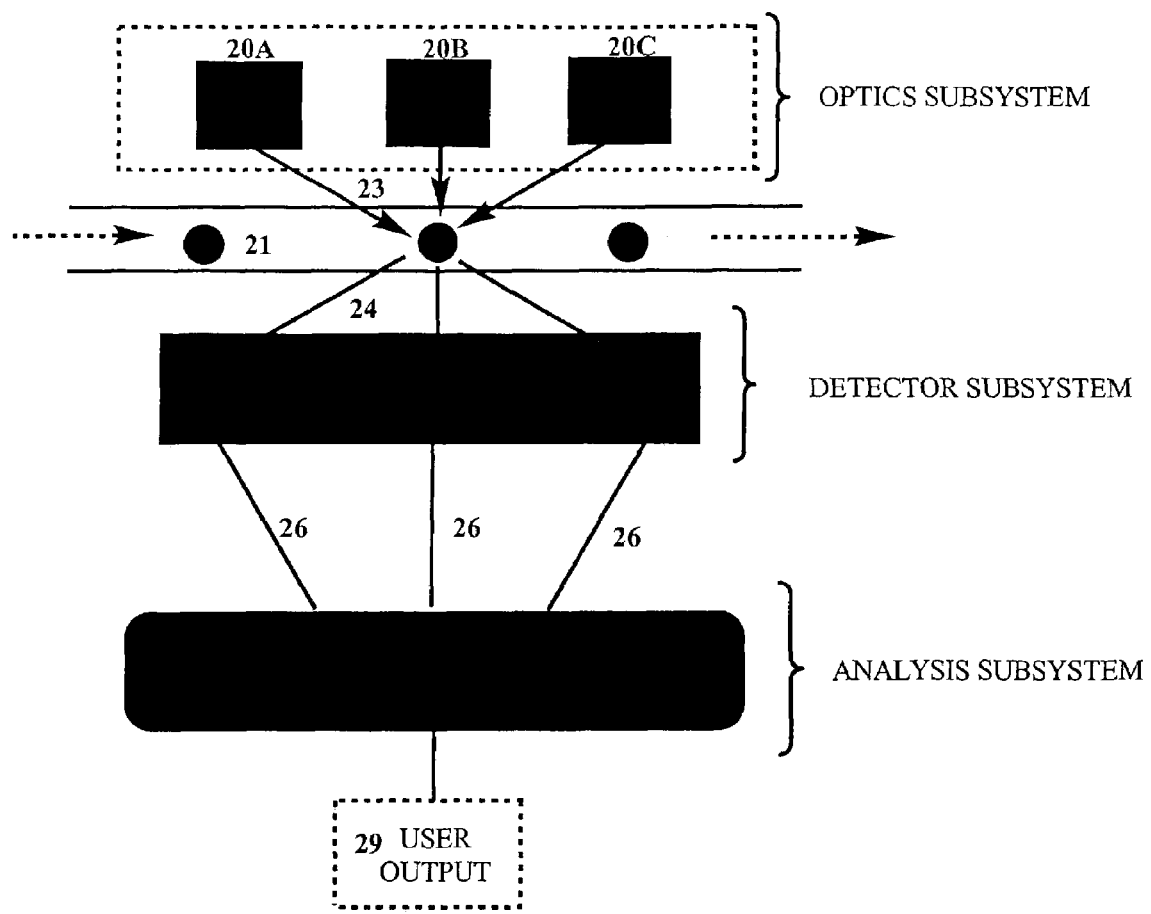
FIG. 3 is a schematic illustration of an exemplary flow cytometry system in accord with the present invention.
Figure 4:
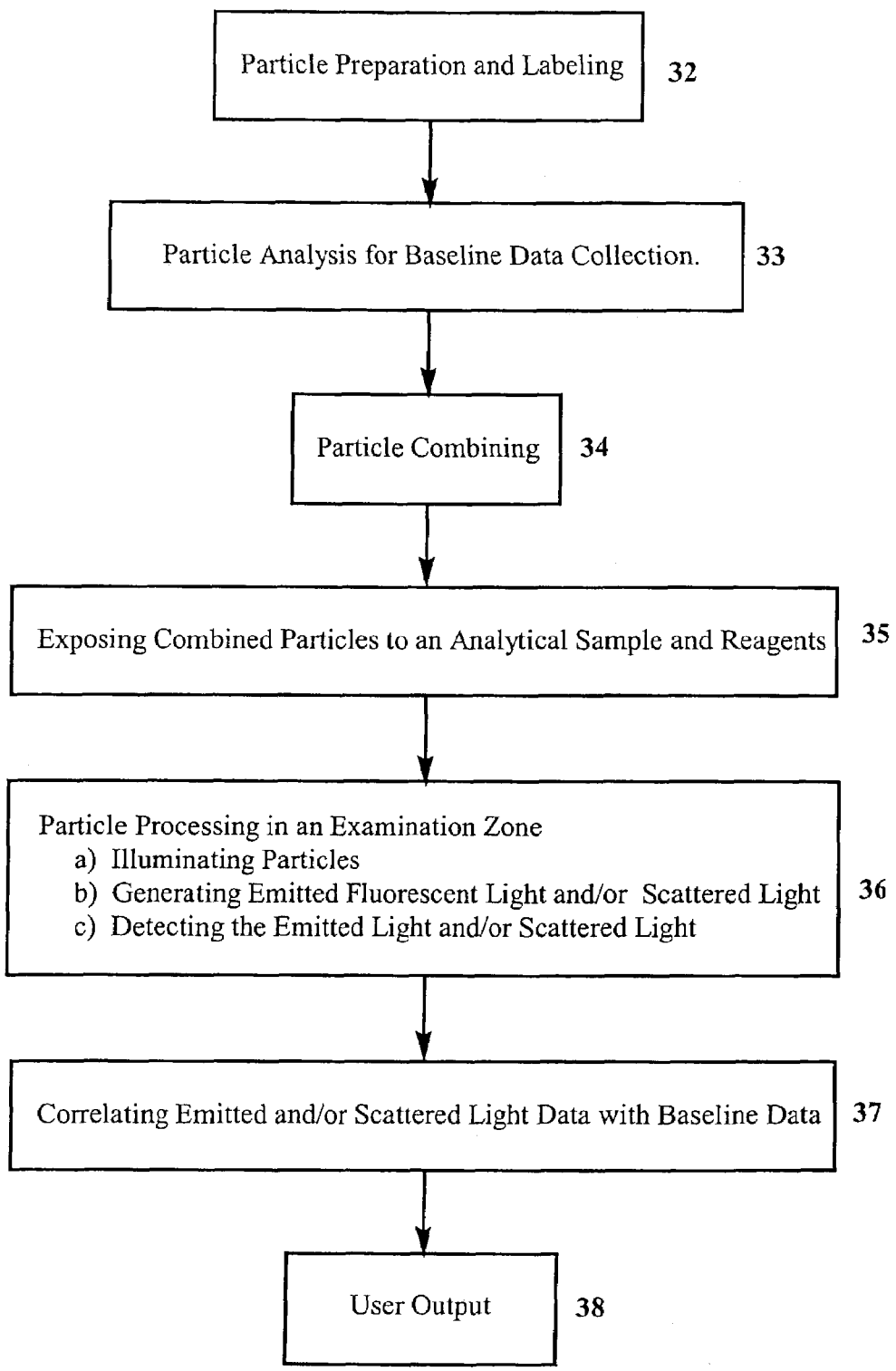
FIG. 4 is a flow chart of a method practiced using the bead detection system as exemplified in FIG. 2 and incorporating the present invention.

FIG. 3 is an exemplary schematic illustration of a flow cytometry system that can be used in the present invention. Light energy 23 is provided in the flow cytometer by exciting light sources 20A, 20B and 20C, such as a laser or an arc lamp, in the optics subsystem. Preferably, a longer wavelength excitation laser is used to simultaneously excite the fluorescent labels, used to mark the beads 21, and one or more shorter wavelength excitation lasers are used to excite the fluorescent analyte detection dyes. The optics subsystem of the cytometry device can include appropriate laser line filters, beam expanders, mirrors, lenses, and flowcells, as well as other components advantageous in operating a cytometry device as will be understood by those with skill in the art with reference to this disclosure.

Appropriate lower wavelength lasers for excitation of the analyte dyes are known to those skilled in the art. A preferred excitation wavelength for the fluorescent analyte detection dyes is a 635 nm diode laser, alternatively, a 650 nm diode laser, or a 633 nm helium-neon laser can be used. Alternatively, a lower wavelength 488 nm argon-ion, or a 530 nm doubled YAG laser can be used. In another aspect of the invention, multiple detection lasers can be used to detect multiple fluorescent dyes at different excitation wavelengths. In this aspect of the invention, a combination of a higher wavelength laser with a lower wavelength laser is used. An example of this aspect of the invention is a 650 nm laser and a 530 nm laser, used to excite different fluorescent dyes on different beads. Longer wavelength lasers (e.g., greater than 750 nm) are known to those skilled in the art. A preferred laser excitation wavelength is about 785 nm. In a preferred, but not required aspect of the invention, a flow cytometry system with three lasers at 532, 650, and 780 nm is used.

Appropriate detectors 25 for detecting a particular emitting light 24 in the detection subsystem are known as will be understood by those with skill in the art with reference to this disclosure. The detectors can be photodiodes or photomultipliers or similar devices that convert light signals into electrical impulses thereby associating the detected light with its fluorescent source. Detectors for detecting forward and side scattered light are known to those in the art and can be used to detect light scatter in the detection system as will be understood by those with skill in the art with reference to this disclosure. Light scatter and fluorescence can be simultaneously detected with respect to each bead in the examination zone. In a preferred, but not required, aspect of the invention, a forward scatter detector, a side scatter detector, and photomultiplier tubes are employed in a detection subsystem. The detection subsystem can also employ a system of filters, mirrors, as well as other components advantageous in operating a cytometry device as will be understood by those with skill in the art with reference to this disclosure. The electrical signals from the detectors 26 are typically fed into the electronics of the system for signal and display processing, storage, and/or further processing.

In an analysis subsystem, hardware, such as a microprocessor 27 in combination with memory storage 28 such as a hard drive in a computer, collects detected data and processes the data. Suitable hardware used in the analysis system is known as will be understood by those with skill in the art with reference to this disclosure. The analysis system software, used for data and signal processing, can correlate detected data with known data to produce analytical results. The analysis subsystem can collect data from the electrical signals associated with each bead. A class of beads is established based on the common characteristics of the class of beads. The data from a known class of beads can be compared to the data detected from sample beads of an unknown class. The processed data and interpreted results can be given as output 29 to a user.

The foregoing is meant to illustrate, but not to limit, the scope of the invention. Indeed, those of ordinary skill in the art can readily envision and produce further embodiments, based on the teachings herein, without undue experimentation.

EXAMPLE I

The fluorescent sensor of the formula (5) was prepared as described in detail below.

Preparation of N-benzyl-hexane-1,6-diamine

A solution of hexamethlene-1,6-diamine (17.15 g, 148 mmol) and benzaldehyde (3.0 ml, 29.5 mmol) in tetrahydrofuran (THF) (300 ml) and ethanol (75 ml) was stirred at room temperature for 24 hours under a nitrogen atmosphere. The solvent was removed and the oil was dried under vacuum. The dried residue was dissolved in THF (100 ml) and sodium borohydride (5.58 g, 148 mmol) was added to the solution. The solution was stirred at room temperature for 7 hours under nitrogen atmosphere. Methanol and water were added to the solution and the solvents were removed under vacuum. The obtained oil was dissolved in chloroform, and washed with water. The solution was dried over magnesium sulphate and the solvent was then removed under vacuum to give a colorless oil (4.49 g, 74%). $^1$H NMR (CDCl$_3$) δ/ppm 1.1-1.5 (8H, m, (CH$_2$)$_4$), 2.55 (2H, t, NHCH$_2$), 2.65 (2H, t, ArCNCH$_2$), 3.75 (2H, s, ArCH$_2$), 7.1-7.25 (5H, m, ArH).

Preparation of N-benzyl-N'-pyren-1-ylmethylene-hexane-1,6-diamine

A solution of N-benzyl-hexane-1,6-diamine (500 mg, 2.42 mmol) and 1-pyrenecalboxaldehyde (670 mg, 2.90 mmol) in THF and methanol (12.5 ml each) was stirred at room temperature for 20 hours under a nitrogen atmosphere. The solvent was removed under vacuum, and the residue was washed with methanol. The precipitate was filtered off, the filtrate was removed and dried under vacuum to give a yellow oil (940 mg, 93%). $^1$H NMR (CDCl$_3$) δ/ppm 1.45-1.62 (6H, m, (CH$_2$)$_3$), 1.85 (2H, m, =HCCH$_2$), 2.65 (2H, t, NHCH$_2$), 3.78 (2H, s, PhCH$_2$), 3.85 (2H, t, =NCH$_2$), 7.15-7.25 (5H, m, Ph-H), 7.95-8.23, 8.53, 8.88 (7H, 1H, 1H respectively, m, d, d, Py-H), 9.27 (1H, s, N=CH). $^{13}$C NMR (CDCl$_3$) δ/ppm 27.31, 27.49, 30.12, 31.16, 49.50, 54.13, 62.77, 122.64, 125.00, 125.59, 125,84, 126.12, 126.24, 126.91, 127.50, 128.16, 128.42, 128.59, 130.64, 131.30, 140.50, 159.54; m/z (TOF) 419 ([M+H]$^+$, 100%).

Preparation of N-benzyl-N'-pyren-1-ylmethyl-hexane-1,6-diamine

A solution of N-benzyl-N'-pyren-1-ylmethylene-hexane-1,6-diamine (420 mg, 1.00 mmol) and sodium borohydride (190 mg, 5.00 mmol) in methanol (10.0 ml) was stirred at room temperature for 3 hours under a nitrogen atmosphere. The solvent was removed under vacuum, and the residue was dissolved in chloroform and washed with water, and dried over magnesium sulphate. The solvent was removed and the residue was dried under vacuum to give a yellow oil (386/mg, 92%). $^1$H NMR (CDCl$_3$) δ/ppm 1.32 (4H, m, (CH$_2$)$_2$), 1.45 (2H, m, BnNCCH$_2$), 1.55 (2H, m, PyCNCCH$_2$), 2.55 (2H, t, BnNCH$_2$), 2.75 (2H, t, PyCNCH$_2$), 3.75 (2H, s, PhCH$_2$), 4.50 (2H, s, PyCH$_2$), 7.15-7.25 (5H, m, Ph-H), 7.95-8.10, 8.15-8.22, 8.37 (4H, 4H, 1H respectively, m, m, d, Py-H). $^{13}$C NMR (CDCl$_3$) δ/ppm 27.35, 30.16, 49.46, 50.02, 51.94, 54.13, 54.13, 123.19, 124.72, 125.00, 125.09, 125.89, 126.89, 127.03, 127.50, 127.64, 128.14, 128.40, 129.06, 131.34, 134.15; m/z (EI) 420 ([M])+, 7%).

Preparation of N-benzyl-N,N'-bis-(2-boronobenzyl)-N'-pyren-1ylmethyl-hexane-1,6-diamine (Formula 5).

A solution of N-pyren-1-ylmethyl-hexame-1,6-diamine (291 mg, 0.69 mmol), 2-(2-bromomethyl-phenyl)-[1,3,2]dioxaborinane (422 mg, 1.66 mmol), and potassium carbonate (380 mg, 2.76 mmol) in dry acetonitril (10 ml) was heated at reflux for 20 hours under nitrogen atmosphere. The solvent was removed under vacuum, the residue was dissolved in chloroform and washed with water. The solvent was dried over magnesium sulphate and removed under vacuum. The residue was dissolved in THF (10 ml). Water (10 ml) was added to the THF solution, and the solution was stirred at room temperature for 3 hours. Organic phase was extracted with chloroform, washed with water, and dried over magnesium sulphate. The solvent was removed under vacuum. The residue was reprecipitated from chloroform with n-hexane to give a white yellow powder (172 mg, 35%). $^1$H NMR (CDCl$_3$) δ/ppm 1.25-1.48 (8H, m, (CH$_2$)$_4$), 2.25 (2H, t, BnNCH$_2$), 2.48 (2H, t, PyCNCH$_2$), 3.45 (2H, s, PhB(OH)CH$_2$NBn), 3.58 (2H, s, PhB(OH)CH$_2$NCPy), 3.85 (2H, s, PhCH$_2$), 4.21 (2H, s, PyCH$_2$), 7.02-7.41 and 7.88-8.19 (22H, m, Ar—H), 8.86 (4H, bs, BOH). $^{13}$C NMR (CDCl$_3$) δ/ppm 51.69, 52.99, 54.42, 56.42, 57.11, 61.03, 61.86, 67.85, 122.90, 124.55, 124.99, 125.79, 127.31, 128.28, 128.57, 129.43, 130.00, 130.55, 136.32, 141.56; Found: C, 76.56; H, 6.69; N, 3.80, C$_{44}$H$_{46}$B$_2$N$_2$O$_4$ requires C, 76.76; H, 6.73; N, 4.07%; m/z (FAB) 1230 ([M+H+4(3-HOCH$_2$C$_6$H$_4$NO$_2$)—4(H$_2$O)]+, 100%); mp. 165-168° C.

EXAMPLE II

A relative fluorescent intensity of the sensor of formula (5), as prepared in EXAMPLE I, was measured in 52.1 wt % methanol and phosphate buffer (pH 8.21) with various D-glucose concentrations (FIG. 3). Phosphate buffer was prepared as described in D. D. Perrin, and B. Dempsey, *Buffers for pH and Metal Ion Control*, Chapman and Hall, London, 1974. The fluorescence spectra were recorded as increasing amounts of D-glucose were added to the solution. The mixture solutions were measured excitation at 342 nm. The fluorescent intensity was found to correlate with total D-glucose concentration in the solution.

EXAMPLE III

Preparation of Beads with Glucose Binding Sensor (Prospective Example)

The preparation of a glucose binding sensor to beads is illustrated in detail in FIG. 1. The beads are 5.6 micrometer diameter poly (styrene/5.5% divinyl benzene/5% methacrylic acid), available from Bangs, Laboratories, Inc. of Fishers, Ind. Compound 2 illustrated in FIG. 1 is prepared by stirring a suspension of cross-linked carboxylate modified polymer beads (200 mg), 1,3-diisopropylcarbodiimide (DIPC) (170 mg), 1-hydroxy-1H-benzotriazol (HOBt) (200 mg,), 4-N,N-dimethylaminopyridine (DMAP) (8 mg) in N,N-dimethylformamide (DMF) (5 ml) on an ice bath under nitrogen atmosphere for 30 minutes. Next, bis(hexamethylene) triamine (1.0 g) is added to the solution and stirred at room temperature for 1 day. This reaction mixture is poured into tetrahydrofuran (THF) and stirred for 1 h at room temperature. The mixture is centrifuged to settle the beads, the supernatant was decanted, and the beads are resuspend in methanol. The beads are washed by being centrifuged again, decanting the supernatant, and resuspending the beads in methanol.

Compound 3 is prepared by first stirring a suspension of compound 2 (200 mg) and benzaldehyde (50 mg) in THF and methanol (7 ml each) at room temperature for 5 hours. Sodium borohydride (57 mg) is added to the reaction and stirred at room temperature for 1 hour. The solvent is removed under reduced pressure and the residue is suspended in chloroform. The suspension is washed with water, dried over magnesium sulfate, and the solvent is removed under reduced pressure. The residue is washed twice in methanol by centrifugation, decanting, and resuspension.

Compound 1 is prepared by heating a suspension of compound 3 (95 mg), potassium carbonate (116 mg) and 2-(2-bromobenzyl)-1,3-dioxa-2-borinane (93 mg) in THF (5 ml) and acetonitrile (3 ml) at reflux for 7 h. The mixture is cooled to room temperature, and the supernatant is removed under reduced pressure. The residue was suspended in chloroform and washed with water. The mixture is dried over magnesium sulfate, and then the solvent was removed under reduced pressure. The residue is resuspended in chloroform and n-hexane, and washed by centrifuging and decanting. The washed beads are resuspended in 50 mM Tris buffer adjusted to pH 7.2.

EXAMPLE IV

Competitive Assay Using Glucose Sensing Beads (Prospective Example)

Reaction mixtures are formed by combining approximately 5000 of the beads, 130 nanograms of the glucose analogue fluorescein di-(β-D-glucopyranoside) (Sigma-Aldrich Company, St. Louis, Mo.), and 20 microliters sample suspected to contain glucose in 180 microliters of 50 mM Tris buffer, pH 7.2 with 0.01% Tween 20. The sensor covered beads bind the analyte or its analog. Optionally, added glucose can be used to shift the assay signal range. This is useful but not required. The reaction mixtures are read using a Beckman Coulter EPICS XL flow cytometer with triggering on FS, gating on the beads, and using the FL1 detection channel.

For the same purpose, variations of the assay can also be performed with fluorescently labeled [2-[2-[2-mercapto-(1,2-propanediol)-3-[(1,3-dihydro-3-3-dimethyl-1-propyl-2H-indol-2-ylidine)ethylidine]-1-cyclohexen-1-yl]ethenyl]3,3-dimethyl-1-propylindolium]iodide. The structure of this propane diol ring-locked cyanine dye is shown below.

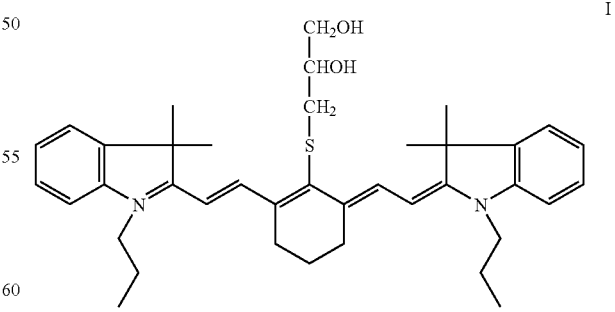

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar feature.

Any element in a claim that does not explicitly state "means" for performing a specified function or "step" for performing a specified function, should not be interpreted as a "means" or "step" clause as specified in 35 U.S.C. '112.

What is claimed is:

1. An analytical system for detecting a saccharide comprising:
   a) a sample known to contain or suspected of containing a saccharide;
   b) one or more than one solid substrate, the solid substrate having attached thereto one or more than one saccharide sensor, the sensor having the formula:

$$Z-(CH_2)_n-N\begin{matrix}(CH_2)_m-Bd_1\\ \\ Sp\\ \\ N-(CH_2)_x-An-Substrate\\ |\\ (CH_2)_y-Bd_2\end{matrix}$$

the saccharide sensor does not contain a fluorophore in its molecular structure;
   Z is selected from the group consisting of hydrogen, alkyl groups, and aryl groups;
   $B_{d1}$ and $B_{d2}$ are independently selected binding groups;
   N is a nitrogen atom;
   Sp is an aliphatic spacer;
   An is an anchor group for attaching the sensor to the solid substrate; and
   n=1 or 2, m=1 or 2, y=1 or 2, and x is an integer; and
   c) means for detecting one or more than one saccharide that is bound to the sensor or saccharide that is not bound to the sensor.

2. The system of claim 1 further comprising a labeled glucose analogue that competes with glucose for binding with the saccharide sensor.

3. The system of claim 1, wherein the solid substrate is one or more than one bead having identification labels comprising:
   a) a fluorescent analyte detection dye, the analyte detection dye being capable of being excited by light at a first excitation wavelength and capable of emitting light at a peak wavelength when excited, and
   b) two or more than two fluorescent labels in a first combination of relative amounts, the fluorescent labels being capable of being excited by light of a same second excitation wavelength and capable of emitting lights at first and second peak wavelengths, distinguishable from each other, respectively, wherein the peak wavelength of the emitted light of the analyte detection dye is different from the first and second maximum wavelengths of the emitted lights of the fluorescent labels by at least 100 nm, and the first and second peak wavelengths differ by at least 100 nm and one of the excitation wavelengths is greater than about 750 nm.

4. The system of claim 3 wherein the means for detecting the particle and saccharide in the sample comprises:
   a) means for exciting the fluorescent dye;
   b) means for exciting the first and second fluorescent labels;
   c) means for detecting the emitted lights; and
   d) means for correlating the detected emitted lights with a particular bead under analysis.

5. The system of claim 3 wherein the analyte detection dye is externally complexed to the outside of the bead, and the fluorescent labels are embedded within the bead.

6. The system of claim 3 wherein the fluorescent labels are both cyanine dyes having emitting lights greater than 750 nm.

7. The system of claim 3 wherein light at the first excitation wavelength causes substantially no emitted light by the fluorescent labels and light at the second excitation wavelength causes substantially no emitted light by the analyte detection dye.

8. A saccharide sensing substrate, comprising
   a solid substrate; and
   a saccharide sensor attached to the substrate having the formula:

$$Z-(CH_2)_n-N\begin{matrix}(CH_2)_m-Bd_1\\ \\ Sp\\ \\ N-(CH_2)_x-An-Substrate\\ |\\ (CH_2)_y-Bd_2\end{matrix}$$

wherein:
   Z is selected from the group consisting of hydrogen, alkyl groups, and a phenyl group;
   N is a nitrogen atom;
   $B_{d1}$ and $B_{d2}$ are independently selected binding groups, wherein the binding groups are capable of binding a saccharide molecule;
   Sp is an aliphatic spacer;
   An is an anchor group for attaching the sensor to the bead; and
   n=1 or 2, m=1 or 2, y=1 or 2 and x is an integer.

9. The saccharide sensing substrate of claim 8, wherein $B_{d1}$ is $R_1-B(OH)_2$ and $B_2$ is $R_2-B(OH)_2$, $B_{d1}$ and $B_2$ are capable of binding a saccharide molecule to form a stable 1:1 complex, and $R_1$ and $R_2$ are aliphatic or aromatic functional groups selected independently from each other and B is a boron atom.

10. The saccharide sensing substrate of claim 9, wherein $R_1$ and $R_2$ are selected from the group consisting of: methyl, ethyl, propyl, butyl, phenyl, methoxy, ethoxy, butoxy, and phenoxy groups.

11. The saccharide sensing substrate of claim 8, wherein Sp is a straight-chain alkane.

12. The saccharide sensing substrate of claim 11, wherein the straight-chain alkane comprises from 1 to 9 carbon atoms.

13. The saccharide sensing substrate of claim 12, wherein the straight-chain alkane comprises 6 carbon atoms.

14. The saccharide sensing substrate of claim 8, wherein the saccharide sensor attached to the solid substrate has the following general structure:

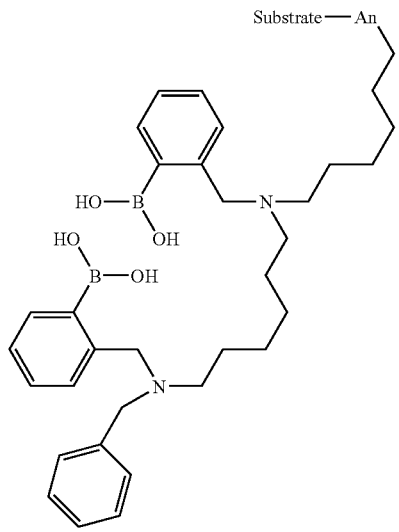

wherein An is an anchor group for attaching the sensor to the solid substrate.

15. The saccharide sensing substrate of claim 8, wherein the sensor attached to the solid substrate has the following general structure:

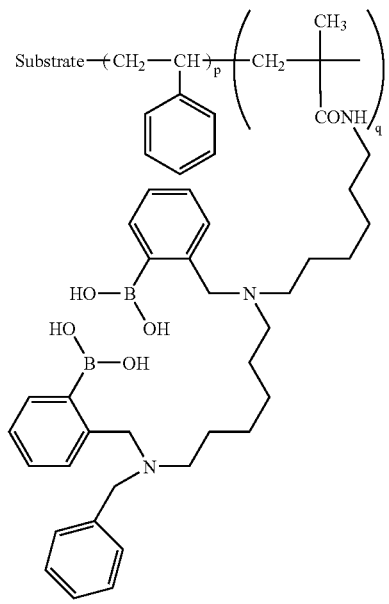

wherein p and q are integers and the ratio of p/q is one or greater than one.

16. The saccharide sensing substrate of claim 8, wherein $B_{d1}$, $B_{d2}$, Sp, m, and q are chosen to provide selective binding of the saccharide sensor to glucose.

17. The substrate of claim 8, wherein the saccharide sensor is a glucose binding sensor and the saccharide sensing substrate has the formula:

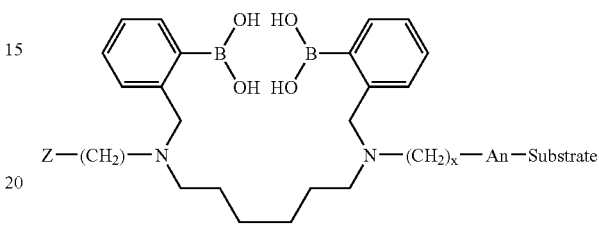

wherein An is an anchor group that attaches the glucose binding sensor to the substrate, Z is selected from the group consisting of hydrogen, alkyl groups, and a phenyl group, and x is an integer.

18. An analytical system for detecting a saccharide comprising:
a) a sample known to contain or suspected of containing a saccharide;
b) one or more than one solid substrate, the solid substrate having attached thereto one or more than one saccharide sensor having the formula:

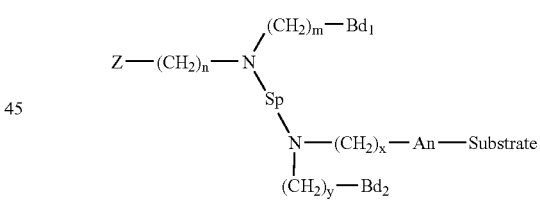

wherein:
Z is selected from the group consisting of hydrogen, alkyl groups, aryl groups and fluorophores;
$B_{d1}$ and $B_{d2}$ are independently selected binding groups;
N is a nitrogen atom;
Sp is an aliphatic spacer;
An is an anchor group for attaching the sensor to the solid substrate; and
n=1 or 2, m=1 or 2, y=1 or 2, and x is an integer; and
wherein the solid substrate is one or more than one bead having identification labels comprising: two or more than two fluorescent labels in a first combination of relative amounts, the fluorescent labels being capableof being excited by light of a same excitation wavelength and capable of emitting lights at first and second peak wavelengths, distinguishable from each other, respectively, the first and second peak wavelengths differ by at least 30; and c) means for detecting the identification labels and the one or more than one saccharide that is bound to the sensor or saccharide that is not bound to the sensor.

19. The analytical system of claim 18, wherein Z is selected from the group consisting of hydrogen, alkyl groups and a phenyl group.

20. The analytical system of claim 19, the system further comprising a labeled glucose analog that competes with glucose for binding with the saccharide sensor.

21. The system of claim 20 wherein the labeled glucose analog is a propane diol ring-locked cyanine dye having the formula:

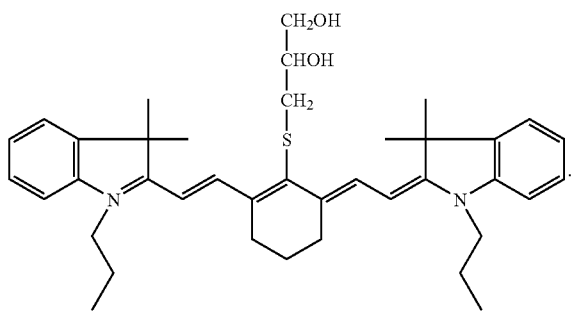

22. The system of claim 18, wherein Z is a fluorophore.

* * * * *